(12) United States Patent
Van Baren et al.

(10) Patent No.: US 6,387,630 B1
(45) Date of Patent: May 14, 2002

(54) METHODS FOR DIAGNOSING MULTIPLE MYELOMA BY DETERMINING REJECTION ANTIGEN PRECURSORS

(75) Inventors: Nicolas Van Baren; Francis Brasseur; Thierry Boon-Falleur, all of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/705,160

(22) Filed: Nov. 2, 2000

Related U.S. Application Data

(60) Division of application No. 09/183,931, filed on Oct. 30, 1998, now Pat. No. 6,210,886, which is a continuation-in-part of application No. 09/018,422, filed on Feb. 4, 1998, now Pat. No. 5,985,571.

(51) Int. Cl.[7] .......................... C12Q 1/68; C12P 19/34; G01N 33/53; G01N 33/574
(52) U.S. Cl. .......................... 435/6; 435/91.2; 435/7.1; 435/7.23
(58) Field of Search .......................... 435/6, 91.2, 7.1, 435/7.23

(56) References Cited

U.S. PATENT DOCUMENTS

| | | | |
|---|---|---|---|
| 5,342,774 A | 8/1994 | Boon et al. | |
| 5,405,940 A | 4/1995 | Boon et al. | |
| 5,512,444 A | 4/1996 | Patard et al. | |
| 5,612,201 A | 3/1997 | DePlaen et al. | |
| 5,985,571 A | * 11/1999 | Baren et al. | 435/6 |
| 6,165,725 A | * 12/2000 | Baren et al. | 435/6 |
| 6,210,886 B1 | * 4/2001 | Baren et al. | 435/6 |
| 6,221,593 B1 | * 4/2001 | Boon-Falleur et al. | 435/6 |

FOREIGN PATENT DOCUMENTS

WO   PCT/US92/04354   3/1992

OTHER PUBLICATIONS

Braseur et al. "Human gene MAGE–1, which codes for a tumor rejection antigen, is expressed by some breast tumors", Int. J. Cancer 52:8:39–841 (1992).

De Plaen et al. "Structures, Chromosomal Location and Expression of 12 Genes of the MAGE Family," Immunogenetics 40:360–369 (1994).

Gaugler et al., "Human Gene MAGE–3 Codes for an Antigen Recognized on a Melanoma by Autologous Cytolytic T Lymphocytes," 8:6:419–427 (1989).

* cited by examiner

Primary Examiner—W. Gary Jones
Assistant Examiner—Joyce Tung
(74) Attorney, Agent, or Firm—Fulbright & Jaworski, LLP

(57) ABSTRACT

Methods for diagnosing multiple myeloma are disclosed. These methods are based upon the observation that tumor rejection antigen precursors are expressed in multiple myeloma. By assaying bone marrow samples, one can diagnose multiple myeloma, and also monitor the disease's progress. Therapeutic approaches to multiple myeloma are also disclosed.

10 Claims, 1 Drawing Sheet

FIG. 1

Multiple Myeloma (MM) staging system (Durie and Salmon)

STAGE I - All of the following criteria

1 - Hemoglobin value > 10 g/100 ml
2 - Serum calcium value normal ≤ 12 mg/100 ml
3 - On roentgenogram, normal bone structure (scale O) or solitary bone plasmacytoma only
4 - Low M-component production rates a) IgG value < 5 g/100 ml
    b) IgA value < 3 g/100 ml
    c) urine light chain M-component on electrophoresis < 4g/24 h.

STAGE II - Fitting neither stage I nor Stage III

STAGE III - One or more of the following criteria

1 - Hemoglobin value < 8.5 g/100 ml
2 - Serum calcium value > 12 mg/100 ml
3 - Advanced lytic bone lesions scale 3
4 - High M-component production rates a) IgG value > 7 g/100 ml
    b) IgA value > 5 g/100 ml
    c) Urine light chain M-component on electrophoresis > 12 g/24 h.

Subclassification :

A = relatively normal renal function (serum creatinine value < 2.0 mg/100 ml)
B = abnormal renal function (serum creatinine value ≥ 2.0 mg/100 ml)

METHODS FOR DIAGNOSING MULTIPLE MYELOMA BY DETERMINING REJECTION ANTIGEN PRECURSORS

RELATED APPLICATION

This application is a divisional application of U.S. application Ser. No. 09/183,931 having a filing date of Oct. 30, 1998 now U.S. Pat. No. 6,210,886B1, which is a continuation in part of Ser. No. 09/018,422, filed on Feb. 4, 1998, now U.S. Pat. No. 5,985,571, which are hereby incorporated by reference herein in their entireties.

FIELD OF THE INVENTION

This invention relates to cancer diagnosis. More particularly, it relates to members of the "tumor rejection antigen precursor" family. Various tumor rejection antigen precursors, including MAGE-1, 2, 3, 4, 6, 10 and 12, BAGE, GAGE 1, 2, 3 and 6, LAGE-1, NY-ESO-1, and PRAME have been identified as being expressed by multiple myeloma.

BACKGROUND AND PRIOR ART

The study of the recognition or lack of recognition of cancer cells by a host organism has proceeded in many different directions. Understanding of the field presumes some understanding of both basic immunology and oncology. Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of turn antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that turn variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanskietal., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce tutu-variants. Since the tum⁻ phenotype differs from that of the parent cell line, one expects a difference in the DNA of tum⁻ cell lines as compared to their tum+ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application and incorporated by reference, teaches a family of human tumor rejection antigen precursor coding genes, referred to as the MAGE family, including MAGE-1, 2, 3, 4, 6 and 12.Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. A U.S. application corresponding in part to this PCT application has issued as U.S. Pat. No. 5,342,774, and is incorporated by reference herein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that, in some cases a nonapeptide is presented on the surface of tumor cells, and that the presentation of the nonapeptide requires that the presenting molecule be HLA-A1.Complexes of the MAGE-1 tumor rejection antigen (the "TRA" or nonapeptide") leads to lysis of the cell presenting it by cytolytic T cells ("CTLs"). Additional research has correlated other nonapeptides derived from MAGE and genes to HLA-A1 and other MHC class I molecules.

Research presented in, e.g., U.S. Pat. No. 5,405,940, incorporated by reference, showed that, when comparing homologous regions of various MAGE genes to the region of the MAGE-1 gene coding for the relevant nonapeptide, there is a great deal of homology.

The nucleic acid molecules which code for the nonapeptides were also described therein. These nucleic acid molecules were described as also being useful as diagnostic probes for tumor presence.

The patent also shows how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The co-transfectant could be used to determine whether the particular MAGE based TRA is presented by the particular HLA molecule.

Many of the references referred to supra present data on the expression pattern of various MAGE genes in different types of cell lines and tumor tissues. What is evident from these data is that there is no "unifying principle" which allows one to predict which MAGE gene will be expressed by a particular tumor type. Thus, while on one level one can say that MAGE genes are "markers" for tumors, on the level of specific tumor types, the correlation of marker and tumor type is not predictable, and must be determined empirically.

In addition to MAGE, other members of the broad family of tumor rejection antigen precursors have been studied, and found to be expressed by different types of tumors. See, e.g., U.S. Pat. No. 5,571,711 for BAGE, U.S. Pat. No. 5,610,013 for GAGE, U.S. Pat. No. 5,811,519 for LAGE-1, allowed patent application Ser. No. 08/725,182, filed on Oct. 3, 1996 for NY-ESO-1, as well as Chen et al., Proc. Natl. Acad. Sci. USA (1996), and Ser. No. 08/316,231 filed Sep. 30, 1994 for PRAME (previously referred to as DAGE). All of these references are incorporated by reference in their entirety.

In the parent application, it was shown that several members of the MAGE family were expressed by multiple myeloma. The analysis has been extended, and it has now been observed that additional tumor rejection antigen precursors are expressed by multiple myeloma. This is the basis of the invention, which is presented in detail in the disclosure which follows.

BRIEF DESCRIPTION OF THE FIGURES

FIG. 1 presents the standard staging system of Durie and Salmon, Cancer 36(3): 842–854 (1975) incorporated by reference. Also see DeVita et al., Cancer, Principles In Practice of Oncology, 4th Edition, 1995.

DETAILED DESCRIPTION OF PREFERRED EMBODIMENTS

Primers

The following is a list of the primers used in the assays which follow infra:

5'-CGGCCGAAGGAACCTGACCCAG-3' (sense) (SEQ ID NO: 1) and

5'GCTGGAACCCTCACTGGGTTGCC-3' (anti-sense) (SEQ ID NO: 2) for MAGE-A1

5'-AAGTAGGACCCGAGGCACTG-3' (sense) (SEQ ID NO: 3) and

5'-GAAGAGGAAGAAGCGGTCTG-3' (anti-sense) (SEQ ID NO: 4) for MAGE-A2

5'-TGGAGGACCAGAGGCCCCC-3 (sense) (SEQ ID NO: 5) and

5'-GGACGATTATCAGGAGGCCTGC-3' (antisense) (SEQ ID NO: 6) for MAGE-A3

5'-GAGCAGACAGGCCAACCG-3' (sense) (SEQ ID NO: 7) and

5'-AAGGACTCTGCGTCAGGC-3' (anti-sense) (SEQ ID NO: 8) for MAGE-A4

5'-TGGAGGACCAGAGGCCCCC-3' (sense) (SEQ ID NO: 9), and

5'-CAGGATGATTATCAGGAAGCCTGT-3' (antisense) (SEQ ID NO: 10) for MAGE-A6,

5'-CACAGAGCAG CACTGAAGGA G-3' (sense) SEQ ID NO: 11), and

5'-CTGGGTAAAG ACTCACTGTC TGG-3' (antisense) (SEQ ID NO: 12) for MAGE-A10,

5'-CGTTGGAGGTCAGAGAACAG-3' (sense) (SEQ ID NO: 13), and

5'-GCCCTCCACTGATCTTTAGCAA-3' (antisense) (SEQ ID NO: 14) for MAGE-A12;

5'-TGGCTCGTCT CACTCTGG-3' (sense) (SEQ ID NO: 15), and

5'-CCTCCTATTG CTCCTGTTG-3' (antisense) (SEQ ID NO: 16) for BAGE,

5'-GACCAAGACG CTADGTAG-3' (sense) (SEQ ID NO: 17), and

5'-CCATCAGGAC CATCTTCA-3' (antisense) (SEQ ID NO: 18) for GAGE 1 & GAGE-2,

5'-GACCAAGGCG CTATGTAC-3' (sense) (SEQ ID NO: 19), and

5'-CCATCAGGAC CATCTTCA-3' (antisense) (SEQ ID NO: 20) for GAGE 3 & GAGE 6,

5'-GCAGGATGGA AGGTGCCC-3' (sense) (SEQ ID NO: 21), and

5'-CTGGCCACTC GTGCTGGGA-3' (antisense) (SEQ ID NO: 22) for LAGE-1,

5'-CCCCACCGCT TCCCGTG-3' (sense) (SEQ ID NO: 23), and

5'-CTGGCCACTC GTGCTGGGA-3' (antisense) (SEQ ID NO: 24) for NY-ESO-1, and

5'-CTGTACTCAT TTCCAGAGCC AGA-3' (sense) (SEQ ID NO: 25), and

5'-TATTGAGAGG TTTCCAAGGG GTT-3' (antisense) (SEQ ID NO: 26) for PRAME

The primers were chosen so that each was in a different exon. Hence, if contaminating genomic DNA was present, the amplification product would be larger.

SEQ ID NO: 11 is new. SEQ ID NOS: 1–10 and 12 may be found in, e.g., DePlaen et al., Immunogenetics 40: 360–369 (1994) incorporated by reference. See. Boel et al., Immunity 2: 167–175 (1995) for SEQ ID NOS: 15 & 16, Vanden Eynde, et al., J. Exp. Med 128: 689–698 (1995), for SEQ ID NOS: 17–20, Lethe. et al., Int. J. Canc. 76: 903–908 (1998), for SEQ ID NOS: 21–24, and Ikeda. et al., Immunity 6: 199–208 (1997) for SEQ ID NOS: 25 & 26.

EXAMPLE 1

PCR assays were carried out using the above referenced primers, generally following DePlaen et al., Immunogenetics 40: 360–369 (1994), and Patard et al., Int J. Cancer 64: 60–64 (1995), both of which are incorporated by reference. Specifically, each PCR reaction used 5 ul of cDNA, obtained as described infra, supplemented with 5 ul of 10×PCR buffer, 1 ul each of 10 mM dNTP, 0.5 ul each of 80 uM solutions of primers, 3 ul of 25 mM MgCl$_2$ 1.25 units of Taq polymerase, and water to bring the reaction volume to 50 ul.

Mixtures were then heated to 94° C. for five minutes, followed by thermocycling for 30 cycles. For MAGE-1, one cycle was one minute at 94° C. followed by three minutes at 72° C. For MAGE-2, a cycle was one minute at 94° C., followed by two minutes at 67° C., and two minutes at 72° C. For MAGE-3, a cycle was one minute at 94° C. and four minutes at 72° C. For MAGE-4, a cycle was one minute at 94°, two minutes at 68° C., and two minutes at 72° C. For MAGE-6, one cycle was one minute at 94° C., followed by two minutes at 70° C. and two minutes at 72° C. For MAGE 10, thirty two cycles were carried out, where one cycle was 1 minute at 94° C. 2 minutes at 62° C., and 3 minutes at 72° C. For MAGE-12, 32 cycles were carried out, each cycle being one minute at 94° C., two minutes at 62° C., and three minutes at 72° C. For BAGE, GAGE, LAGE, NY-ESO-1 and PRAME, the mixtures were heated to 94° C. for only 4 minutes. BAGE amplification involved 30 cycles of 94° C. for 1 minute, 62° C. for 2 minutes, and 72° C. for 2 minutes. For GAGE 1 & 2, 30 cycles were carried out, each cycle consisting of 94° C. for 1 minute, 56° C. for 2 minutes, and 72° C. for 2 minutes . For GAGE 3 & 6, 30 cycles of 94° C. for 1 minute, 58° C. for 2 minutes, and 72° C. for 2 minutes, were carried out . For LAGE-1, 30 cycles of 94° C. for 1 minute, 62° C. for 1 minute, and 72° C. for 2 minutes were carried out. For NY-ESO-1, 30 cycles of 94° C. for 1 minute, 62° C. for 1 minute, and 72° C. for 2 minutes were carried out. For PRAME, 30 cycles of 1 minute at 94° C., 1 minute at 64° C. , and 2 minutes at 72° C. were carried out.

The primers listed supra were used in PCRS, using conditions listed supra, on multiple myeloma bone marrow samples. For each sample, mononucleated cells from anticoagulated bone marrow or blood were purified, washed three times with culture medium and then phosphate buffered saline. Following centrifugation, a cell pellet was obtained, dried, and stored at −80° C.

Total RNA was extracted from the pellets, using standard methods, and then cDNA was synthesized, following Weynants, et al., Int. J. Cancer 56: 826–829 (1994), incorporated by reference. Following synthesis of cDNA, the above referenced protocols were carried out.

Quantitative assessment of the PCR product was performed visually on an ethidium bromide stained agarose gel. Level of expression was normalized for RNA integrity by taking expression levels of β-actin into account. Intensity of PCR product was compared to that resulting from PCR performed on serial dilutions (1:1, 1:3, 1:9, 1:27) of cDNA taken from one of 3 tumor cell lines used as positive control, i.e., MZ2-MEL for all MAGE except A4 & A12, all GAGE, and BAGE; LB23-SARC for MAGE-A4, and LB373-MEL for all others. A sample was deemed positive if the amount of amplified product was equal to or greater than that obtained with the 1:9 dilution of the reference. The results of the assays are given in greater than that obtained with the 1:9 dilution of the reference. The results of the assays are in Table 1, which follows:

TABLE 1

| | | | | | | RT-PCR results | | | | | | | | | | |
|---|---|---|---|---|---|---|---|---|---|---|---|---|---|---|---|---|
| | patient | | | | previous | MAGE | | | | | | | BAGE | GAGE | | LAGE | NY-ESO | |
| diagnosis | N° | sex | age | idiotype | treatment | A1 | A2 | A3 | A4 | A6 | A10 | A12 | 1 | 1/2 | 3–6 | 1 | 1 | Prame |
| MGUS | 1 | M | 71 | IgGκ | N | – | – | – | – | – | – | – | – | – | – | – | – | – |
| | 2 | M | 62 | IgGλ | N | – | – | – | – | – | – | – | – | – | – | – | – | – |
| | 3 | M | 62 | IgGκ | N | – | – | – | – | – | – | – | – | – | – | – | – | – |
| | 4 | F | 39 | IgGκ | N | – | – | – | – | – | – | – | – | – | – | – | – | – |

TABLE 1-continued

| | patient | | | | previous | \multicolumn{7}{c}{MAGE} | BAGE | \multicolumn{2}{c}{GAGE} | LAGE | NY-ESO | |
| --- | --- | --- | --- | --- | --- | --- | --- | --- | --- | --- | --- | --- | --- | --- | --- | --- | --- | --- |
| diagnosis | N° | sex | age | idiotype | treatment | A1 | A2 | A3 | A4 | A6 | A10 | A12 | 1 | 1/2 | 3–6 | 1 | 1 | Prame |
| | 5 | M | 51 | IgGλ | N | – | – | – | – | – | – | – | – | – | – | – | – | – |
| | 6 | M | 64 | IgGλ | N | – | – | – | – | – | – | – | – | – | – | + | – | – |
| Myeloma | 7 | F | 64 | IgGκ | N | – | – | – | – | – | – | – | – | – | – | – | – | – |
| stage I | 8 | M | 71 | IgGλ | Y | – | – | – | – | – | – | – | – | – | – | – | – | – |
| | 9 | M | 70 | IgAκ | N | – | – | – | – | – | – | – | – | – | – | – | – | – |
| | 10 | M | 65 | IgAλ | N | – | – | – | – | – | – | – | – | – | – | – | – | – |
| | 11 | M | 74 | IgGκ | N | – | – | – | – | – | – | – | – | – | – | – | – | – |
| | 12 | F | 69 | IgAλ | N | – | – | – | – | – | – | – | – | – | – | – | – | – |
| | 13 | M | 62 | IgGκ | N | – | – | – | – | – | – | – | – | – | – | – | – | – |
| | 14 | F | 75 | IgGλ | N | – | – | – | – | – | – | – | – | – | – | – | – | – |
| | 15 | F | 65 | IgGκ | N | – | – | – | – | – | – | – | – | – | – | – | – | – |
| Myeloma | 16 | F | 74 | IgAκ | N | – | – | – | – | – | – | – | – | – | – | – | – | – |
| stage III | 17 | F | 65 | IgGκ | Y | – | – | – | – | – | – | – | – | – | – | – | – | – |
| Myeloma | 18 | M | 62 | IgGκ | Y | – | + | + | + | + | – | – | – | + | + | + | + | + |
| stage III | 19 | M | 87 | λ | N | + | + | + | – | + | – | – | – | + | + | + | + | + |
| | 20 | F | 87 | IgGκ | N | + | – | – | – | + | – | – | – | + | + | – | – | + |
| | 21 | F | 81 | IgGκ | N | + | + | + | – | + | – | + | – | – | – | + | – | – |
| | 22 | M | 56 | κ | Y | – | – | – | – | – | – | – | – | – | – | – | – | – |
| | 23 | M | 72 | IgAκ | Y | – | – | – | – | – | – | – | – | + | + | + | – | + |
| | 24 | F | 84 | IgAλ | N | + | – | – | – | – | – | – | – | + | + | + | + | + |
| | 25 | M | 57 | IgGλ | Y | + | – | + | – | – | – | – | + | + | + | + | + | – |
| | 26 | F | 94 | IgGκ | Y | – | – | – | – | – | – | – | – | + | + | + | – | – |
| | 27 | M | 69 | IgGκ | Y | – | – | – | – | – | – | – | – | – | – | – | – | + |
| | 28 | M | 45 | IgGκ | N | – | – | – | – | – | – | – | – | – | – | – | – | – |
| | 29 | M | 72 | IgAκ | Y | + | + | + | + | + | + | + | + | + | + | + | + | + |
| | 30 | F | 53 | IgGκ | Y | – | – | – | – | – | – | – | – | – | – | + | – | – |
| | 31 | M | 59 | IgAκ | N | + | – | + | – | + | – | + | + | + | + | + | + | – |
| | 32 | M | 59 | IgGκ | Y | – | – | – | – | – | – | – | – | – | – | + | – | – |
| | 33 | M | 61 | IgGκ | Y | – | – | – | – | – | – | – | – | – | – | – | – | – |
| | 34 | F | 66 | λ | Y | – | – | – | – | – | – | – | – | + | + | + | + | + |
| | 35 | F | 84 | IgAκ | N | – | – | – | – | + | – | – | – | + | + | – | – | – |
| | 36 | F | 62 | IgAκ | N | – | – | – | – | – | – | – | – | – | – | – | – | + |
| | 37 | F | 71 | κ | Y | + | + | + | – | + | + | + | + | + | + | + | + | + |
| | 38 | F | 64 | IgAκ | Y | – | – | – | – | – | – | – | – | – | – | – | – | + |
| | 39 | M | 63 | κ | Y | – | – | – | – | – | – | – | – | – | – | + | – | – |
| | 40 | M | | IgGκ | Y | – | – | – | – | – | – | – | – | – | – | – | – | + |
| | 41 | M | 77 | IgAκ | N | – | – | – | – | – | – | – | – | – | – | – | – | – |
| | 42 | F | 56 | IgGκ | Y | – | – | – | – | – | – | – | – | – | – | – | – | + |
| | 43 | M | 53 | IgGκ | Y | – | – | + | + | + | – | – | – | – | – | – | – | + |
| | 44 | M | 61 | | | – | – | – | – | – | – | – | – | – | – | – | – | – |
| Plasma cell | 45 | F | 44 | IgAκ | N | – | – | – | – | – | – | – | – | – | – | + | + | – |
| leukemia | 46 | F | 38 | IgGκ | N | – | – | – | – | – | – | – | – | – | – | – | – | – |

Peripheral blood was used for a few samples, because circulating myeloma cells were identified therein. The results for β-actin were used as a control. It may be useful to note that "% plasma" as used in Table 1 refers to the proportion of malignant plasmocytes following visual analysis of a bone marrow aspirate, via microscopy. In multiple myeloma, the standard range is 15%–100%.

The column making reference to "stage" refers to standard diagnostic parameters for multiple myeloma, following Durie and Salmon, supra, incorporated by reference. These parameters are set forth in FIG. 1. All samples with MGUS, stage I or stage II myeloma were negative, except one sample from an MGUS sample which was positive for LAGE-1. A majority of stage III myelomas expressed at least one gene. In terms of frequency, LAGE-1 (52%), PRAME (48%) and GAGE (48%) were expressed most frequently. NY-ESO-1 and MAGE-A6 were both expressed in 31% of samples, while MAGE-A1 and MAGE-A3 were expressed in 28%, MAGE-A2 in 17%, MAGE-A12 and BAGE in 14%, and MAGE-A4 & A10 at 7%.

EXAMPLE 2

One approach to cancer therapy is the use of cytolytic T cells, either autologous or allogeneic, which are specific to complexes of peptides and MHC molecules. These "CTLs" recognize and lyse the cells which present the complexes. It was of interest to determine if CTLs could recognize and lyse myeloma cells. In these experiments, CTL clone 434/1 was used. This line was derived from the blood of a patient who was typed as positive for HLA-a1 positive and was diagnosed with hemochromatosis. To derive the line, blood samples were stimulated repeatedly with autologous, phytohemagglutinin-A simulated T cells, which had been pulsed with an HLA-A1 binding peptide derived from MAGE-3, i.e., EVDP1GHLY (SEQ ID NO: 27). See U.S. Pat. No. 5,405, 940, incorporated by reference.

The CTL was combined with myeloma cell lines EJM and U266, as well as control line MZ2-MEL. These three lines have similar, high expression levels for MAGE-A3, as determined by PCR. (MZ2-MEL is disclosed in, e.g., the '940 patent supra, as well as U.S. Pat. No. 5,342,774. It is a melanoma line). As negative control, HLA-A1 negative myeloma cell line U266 was used.

These target cells were labelled with $^{51}$Cr, washed, dispensed into microwell plates at 1000 cells/well, in Iscove's medium supplemented with 10% human serum and with L-arginine (116 mg/L), L-asparagine (36 mg/L), and L-glutamine (216 mg/L). CTL 434/1 was added at increasing effector (CTL) to target ratios. Cells were centrifuged, incubated at 37° C. for 4 hours, and chromium release determined by measuring radioactivity in the supernatant. A more detailed protocol may be found in Boon, et al., J. Exp. Med 152: 1184 (1980), incorporated by reference.

The result indicated that U266 was not lysed, as expected, while both EJM and MZ2-MEL were lysed. The percentage of cells lysed was essentially identical. Similar results were secured with the peptide FLWGPRALV (SEQ ID NO: 28), also derived from MAGE-3.

EXAMPLE 3

A series of immunohistochemical experiments were then carried out, using EJM and U266, both of which are MAGE-A3 positive, as described supra, the myeloma line "Fravel", which is a MAGE-A3 negative line, as well as cells from gut biopsy taken from a myeloma patient who was receiving chemotherapy, and had developed skin and gut plasmacytomas. The patient had tested positive for MAGE-A3 expressing, stage III myeloma. A bone marrow sample was taken from a different patient with MAGE-A3 expressing stage III myeloma. Finally, a bone marrow cytospin was taken from a patient who had a myeloma in relapse after two autografts.

The myeloma cell lines, and one of the bone marrow cells were washed in Tris buffered saline, and cytospinned at 500 rpm for 4 minutes on microscopic slides ($10^5$ cells/slide). The cells from the bone marrow of the second patient were smeared onto slides. All were air dried at room temperature, wrapped in aluminum foil, and stored at −80° C. until needed.

When tested, they were fixed in 10% buffered formalin at room temperature for 10 minutes, then washed in Tris buffered saline for 2 minutes. They were then incubated with anti-MAGE A3 hydrodoma supernatant (Kocher, et al., Can. Res. 55: 2236 (1995)), undiluted in one case, and diluted 1/10 for others, at 4° C. for 18 hours. Alternatively, an isotype matched irrelevant monoclonal antibody was used. Incubation continued, with bitonylated anti-mouse immunoglobulin and conjugates of alkaline phosphatase and streptavidin. Chromogen was added to stain the samples.

The treatment of the gut biopsy was somewhat different. Samples were formalin fixed, paraffin embedded, and then heated, following deparaffinization in a 1500 Watt microwave oven, at least twice, in citrate buffer for antigen retrieval, for 5 minutes. Then, the samples were washed in Tris buffered saline containing 0.05% Tween 20 for 1 minute and incubated with either the diluted anti-Mage-A3 antibody, or the irrelevant antibody, at room temperature for 1 hour. Biotinylated antimouse immunoglobulin, and peroxidase conjugated polymer backbone were added, with AEC as chromogen.

Approximately 30% of all malignant plasma cells were positive, while normal bone marrow, and the remaining myeloma were negative. Slides incubated with the irrelevant antibody did not stain.

The foregoing data demonstrate the features of the invention. One aspect of the invention is the ability to determine presence of myeloma, multiple myeloma in particular, and especially late stage multiple myeloma, by assaying a sample for expression of a tumor rejection antigen precursor. Most preferably, the sample is a bone marrow sample. While PCR has been exemplified, the artisan of ordinary skill will recognize that any hybridization assay, including nucleic acid amplification assays, may be used. It is especially preferred to use one or more hybridization probes which are specific to one of MAGE 1, 2, 3, 4, 6, 10 or 12, BAGE, GAGE, NY-ESO-1, LAGE or PRAME. These are preferably 17–50 nucleotides in length, more preferably 17–25 nucleotides in length. One can assay for one, or more than one, of the species listed supra. Other TRAP genes may also be expressed by these myeloma cells. "TRAP" encoding nucleic acid molecules, or "MAGE gene", as used herein, refers to any of the genes described in the literature as a TRAP family member. Exemplary but by no means exclusive, are the genes and sequences set forth in U.S. Pat. No. 5,342,774, incorporated by reference, the other patents referred to supra as well as sequences which hybridize to the sequences listed therein under the stringent conditions provided. Also see PCT/US92/04354, also incorporated by reference, and cited supra, as well as DePlaen and Patard, incorporated by reference and cited supra.

Another aspect of the invention is a method for monitoring the course of a therapeutic regime. As will be noted, the TRAP sequences are expressed, for the most part, in late stage, i.e., stage III, myeloma. In the course of treatment (e.g., chemotherapy, immunotherapy, bone marrow transplant, etc.), as myeloma regresses, one can monitor this by noting loss or decrease in TRAP expression relative to a level determined at a prior point in time. Similarly, development of the disease, relapse, response to bone marrow transplant, etc., can be monitored by observing increases. This can be accomplished via, e.g., polymerase chain reaction ("PCR") RT-PCR being preferred or other hybridization assays.

Additional diagnostic methods include assays of precursor T cells or cytolytic T cells specific for complexes of MHC molecules and TRAP derived peptides. These can be determined via, e.g., chromium release, tumor necrosis factor ("TNF"), ELISPOT, soluble complexes of MHC/TRAP peptides labelled, e.g., fluorescently or with some other signaling label, or with multimeric peptide complexes, and so forth. These types of assay are useful before, during, and after the therapeutic treatments described, supra.

The recognition that TRAP molecules are implicated in multiple myeloma has therapeutic ramifications as well. One may, for example, treat the subject in an appropriate way such that cytolytic T lymphocytes recognize and destroy those cells which present tumor rejection antigens on their surface.

For example, it is known that various TRAP-derived peptides function as T cell epitopes, in that they are presented by MHC class I molecules, with the resulting complex being recognized and lysed by cytolytic T cells. Exemplary, but by no means limiting, are the peptides disclosed in U.S. Pat. Nos. 5,405,940, the disclosure of which is incorporated by reference. The ability to provoke proliferation of autologous T cells in vitro, via contact of blood samples to complexes of peptide and MHC molecules is well known. The resulting autologous cytolytic T cells can be reinfused to the subject from whom the blood samples was taken, after which the cytolytic T cells enter the bone marrow. It is known that plasma cells express MHC molecules. See, e.g., Yi et al., Blood 90(5): 1960–1967 (1997), incorporated by reference. Hence, the reinfused CTLs would target the plasma cells which present the MAGE derived peptides on their surface, presenting complexes identical to these used to generate the CTLs in vitro.

It was shown, e.g., that CTLs specific for peptide MHC complexes recognize and lyse myeloma, and that antibodies specific for the expression product of TRAP genes recognize these as well. One can make valid assumptions about the predicted frequence of presentation of peptides derived from tumor rejection antigen precursors, by multiplying probability of having the corresponding gene expressed by the myeloma and the prevalence of the particular HLA allele in the Caucasian population, as per the following:

| gene | HLA | antigenic peptide | position in protein | predicted frequency |
|---|---|---|---|---|
| MAGE-A1 | A1 | EADPTGHSY | 161–169 | 8% |
|  | Cw16 | SAYGEPRKL | 230–238 | 2% |
| MAGE-A2 | A2 | KMVELVHFL | 112–120 | 10% |
|  | A2 | YLQLVFGIEV | 157–166 | 10% |
| MAGE-A3 | A1 | EVDPIGHLY | 168–176 | 8% |
|  | A2 | KVAELVHFL | 112–120 | 16% |
|  | A2 | FLWGPRALV | 271–279 | 16% |
|  | A24 | IMPKAGLLI | 195–203 | 6% |
|  | B44 | MEVDPIGHLY | 167–176 | 7% |
| MAGE-A12 | A2 | FLWGPRALV | 271–279 | 8% |
| BAGE | Cw16 | AARAVFLAL | 2–10 | 1% |
| GAGE-1/2 | Cw6 | YRPRPRRY | 9–16 | 7% |
| PRAME | A24 | LYVDSLFFL | 301–309 | 10% |
| NY-ESO-1 | A2 | SLLMWITQCFL | 157–167 | 18% |
|  |  | SLLMWITQC | 157–165 | 18% |
|  |  | QLSLLMWIT | 155–163 | 18% |

CTLs specific to the relevant complexes, and antibodies to the tumor rejection antigen precursor, can be used to determine these.

Similarly, one can envision treatment methodologies which employ dendritic cells, pulsed with the peptide epitopes alluded to supra, as well as cells which have been treated so as to present relevant complexes on their surfaces. Such cells may be transformed or transfected with a TRAP gene or genes, a TRAP "minigene" or "minigenes", which encodes only relevant MHC binding peptides such as tumor rejection antigens, and/or a relevant MHC-molecule encoding sequence, such as HLA-A1, A2, Cw6, and so forth. If appropriate, such cells may be irradiated prior to administration.

Other features of the invention will be clear to the skilled artisan and need not be set forth herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for determining possible multiple myeloma comprising contacting a cell containing sample taken from bone marrow or blood of a patient with an antibody specific for a tumor rejection antigen precursor associated with multiple myeloma and assaying said cell containing sample for binding of the antibody to cells in said sample, wherein binding of said antibody to said cells in said sample is indicative of possible multiple myeloma in said patient.

2. A method for determining possible multiple myeloma comprising contacting a cell containing sample taken from bone marrow or blood of a patient with a cytolytic T cell which recognizes complexes of a peptide derived from a tumor rejection antigen precursor associated with multiple myeloma and an HLA molecule to which said peptide binds, wherein proliferation of said CTLs or lysis of cells in the cell containing sample is indicative of possible multiple myeloma in said patient.

3. The method of claim 1, wherein said antibody is a monoclonal antibody.

4. The method of claim 1, wherein said antibody is detectably labeled.

5. The method of claim 1, wherein said tumor rejection antigen precursor is LAGE.

6. The method of claim 1, wherein said tumor rejection antigen precursor is PRAME.

7. The method of claim 1, wherein said tumor rejection antigen precursor is GAGE.

8. The method of claim 1, wherein said tumor rejection antigen precursor is NY-ESO-1.

9. The method of claim 1, wherein said tumor rejection antigen precursor is BAGE.

10. The method of claim 1, wherein said tumor rejection antigen precursor is MAGE-A1, MAGE-A2, MAGE-A3, MAGE-A4, MAGE-A6, MAGE-A10, or MAGE-A12.

* * * * *

SEQUENCE LISTING

```
<160> NUMBER OF SEQ ID NOS: 44

<210> SEQ ID NO 1
<211> LENGTH: 22
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 1
cggccgaagg aacctgaccc ag                                              22

<210> SEQ ID NO 2
<211> LENGTH: 23
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 2
gctggaaccc tcactgggtt gcc                                             23

<210> SEQ ID NO 3
<211> LENGTH: 20
<212> TYPE: DNA
<213> ORGANISM: Artificial sequence
<220> FEATURE: PCR primer
<223> OTHER INFORMATION: Synthesized by oligonucleotide synthesis
      achine.

<400> SEQUENCE: 3
aagtaggacc cgaggcactg                                                 20
```

```
<210> SEQ ID NO 4
<211> LENGTH: 20
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 4
gaagaggaag aagcggtctg                                              20

<210> SEQ ID NO 5
<211> LENGTH: 19
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 5
tggaggacca gaggccccc                                               19

<210> SEQ ID NO 6
<211> LENGTH: 22
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 6
ggacgattat caggaggcct    gg                                        22

<210> SEQ ID NO 7
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 7
gagcagacag gccaaccg                                                18

<210> SEQ ID NO 8
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 8
aaggactctg cgtcaggc                                                18

<210> SEQ ID NO 9
<211> LENGTH: 19
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 9
tggaggacca gaggccccc                                               19
```

```
<210> SEQ ID NO 10
<211> LENGTH: 24
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 10
caggatgatt atcaggaagc ctgt                                          24

<210> SEQ ID NO 11
<211> LENGTH: 21
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 11
cacagagcag cactgaagga g                                             21

<210> SEQ ID NO 12
<211> LENGTH: 23
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 12
ctgggtaaag actcactgtc tgg                                           23

<210> SEQ ID NO 13
<211> LENGTH: 20
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 13
cgttggaggt cagagaacag                                               20

<210> SEQ ID NO 14
<211> LENGTH: 22
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 14
gccctccact gatctttagc aa                                            22

<210> SEQ ID NO 15
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 15
tggctcgtct cactctgg                                                 18
```

```
<210> SEQ ID NO 16
<211> LENGTH: 19
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 16
cctcctattg ctcctgttg                                                    19

<210> SEQ ID NO 17
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 17
gaccaagacg ctadgtag                                                     18

<210> SEQ ID NO 18
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 18
ccatcaggac catcttca                                                     18

<210> SEQ ID NO 19
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 19
gaccaaggcg ctatgtac                                                     18

<210> SEQ ID NO 20
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 20
ccatcaggac catcttca                                                     18

<210> SEQ ID NO 21
<211> LENGTH: 18
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 21
gcaggatgga aggtgccc                                                     18

<210> SEQ ID NO 22
```

```
<211> LENGTH: 19
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 22
ctggccactc gtgctggga                                              19

<210> SEQ ID NO 23
<211> LENGTH: 17
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 23
ccccaccgct tcccgtg                                                17

<210> SEQ ID NO 24
<211> LENGTH: 19
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 24
ctggccactc gtgctggga                                              19

<210> SEQ ID NO 25
<211> LENGTH: 23
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 25
ctgtactcat ttccagagcc aga                                         23

<210> SEQ ID NO 26
<211> LENGTH: 23
<212> TYPE: DNA
<213> ORGANISM: Artificial sequence
<220> FEATURE: PCR primer
<223> OTHER INFORMATION: Synthesized by oligonucleotide synthesis
      machine

<400> SEQUENCE: 26
tattgagagg tttccaaggg gtt                                         23

<210> SEQ ID NO 27
<211> LENGTH: 9
<212> TYPE: PRT
<213> ORGANISM: Homo sapiens
<220> FEATURE:
<223> OTHER INFORMATION:

<400> SEQUENCE: 27

Glu Val Asp Pro Ile Gly His Leu Tyr
                5

<210> SEQ ID NO 28
<211> LENGTH: 9
```

```
<212> TYPE: PRT
<213> ORGANISM: Homo sapiens
<220> FEATURE:
<223> OTHER INFORMATION:

<400> SEQUENCE: 28

Phe Leu Trp Gly Pro Arg Ala Leu Val
                5

<210> SEQ ID NO 29
<211> LENGTH: 9
<212> TYPE: PRT
<213> ORGANISM: Homo sapiens
<220> FEATURE:
<223> OTHER INFORMATION:

<400> SEQUENCE: 29

Glu Ala Asp Pro Thr Gly His Ser Tyr
                5

<210> SEQ ID NO 30
<211> LENGTH: 9
<212> TYPE: PRT
<213> ORGANISM: Homo sapiens
<220> FEATURE:
<223> OTHER INFORMATION:

<400> SEQUENCE: 30

Ser Ala Tyr Gly Glu Pro Arg Lys Leu
                5

<210> SEQ ID NO 31
<211> LENGTH: 9
<212> TYPE: PRT
<213> ORGANISM: Homo sapiens
<220> FEATURE:
<223> OTHER INFORMATION:

<400> SEQUENCE: 31

Lys Met Val Glu Leu Val His Phe Leu
                5

<210> SEQ ID NO 32
<211> LENGTH: 10
TYPE: PRT
ORGANISM: Homo sapiens
<220> FEATURE:
<223> OTHER INFORMATION:

<400> SEQUENCE: 32

Tyr Leu Gln Leu Val Phe Gly Ile Glu Val
                5                   10

<210> SEQ ID NO 33
<211> LENGTH: 9
TYPE: PRT
ORGANISM: Homo sapiens
<220> FEATURE:
<223> OTHER INFORMATION:

<400> SEQUENCE: 33

Glu Val Asp Pro Ile Gly His Leu Tyr
                5

<210> SEQ ID NO 34
<211> LENGTH: 9
TYPE: PRT
```

```
ORGANISM: Homo sapiens
<220> FEATURE:
<223> OTHER INFORMATION:

<400> SEQUENCE: 34

Lys Val Ala Glu Leu Val His Phe Leu
                 5

<210> SEQ ID NO 35
<211> LENGTH: 9
TYPE: PRT
ORGANISM: Homo sapiens
<220> FEATURE:
<223> OTHER INFORMATION:

<400> SEQUENCE: 35

Phe Leu Trp Gly Pro Arg Ala Leu Val
                 5

<210> SEQ ID NO 36
<211> LENGTH: 9
TYPE: PRT
ORGANISM: Homo sapiens
<220> FEATURE:
<223> OTHER INFORMATION:

<400> SEQUENCE: 36

Ile Met Pro Lys Ala Gly Leu Leu Ile
                 5

<210> SEQ ID NO 37
<211> LENGTH: 10
TYPE: PRT
ORGANISM: Homo sapiens
<220> FEATURE:
<223> OTHER INFORMATION:

<400> SEQUENCE: 37

Met Glu Val Asp Pro Ile Gly His Leu Tyr
                 5                  10

<210> SEQ ID NO 38
<211> LENGTH: 9
TYPE: PRT
ORGANISM: Homo sapiens
<220> FEATURE:
<223> OTHER INFORMATION:

<400> SEQUENCE: 38

Phe Leu Trp Gly Pro Arg Ala Leu Val
                 5

<210> SEQ ID NO 39
<211> LENGTH: 9
TYPE: PRT
ORGANISM: Homo sapiens
<220> FEATURE:
<223> OTHER INFORMATION:

<400> SEQUENCE: 39

Ala Ala Arg Ala Val Phe Leu Ala Leu
                 5

<210> SEQ ID NO 40
<211> LENGTH: 8
TYPE: PRT
ORGANISM: Homo sapiens
```

```
<220> FEATURE:
<223> OTHER INFORMATION:

<400> SEQUENCE: 40

Tyr Arg Pro Arg Pro Arg Arg Tyr
                5

<210> SEQ ID NO 41
<211> LENGTH: 9
TYPE: PRT
ORGANISM: Homo sapiens
<220> FEATURE:
<223> OTHER INFORMATION:

<400> SEQUENCE: 41

Leu Tyr Val Asp Ser Leu Phe Phe Leu
                5

<210> SEQ ID NO 42
<211> LENGTH: 11
TYPE: PRT
ORGANISM: Homo sapiens
<220> FEATURE:
<223> OTHER INFORMATION:

<400> SEQUENCE: 42

Ser Leu Leu Met Trp Ile Thr Gln Cys Phe Leu
                5                   10

<210> SEQ ID NO 43
<211> LENGTH: 9
TYPE: PRT
ORGANISM: Homo sapiens
<220> FEATURE:
<223> OTHER INFORMATION:

<400> SEQUENCE: 43

Ser Leu Leu Met Trp Ile Thr Gln Cys
                5

<210> SEQ ID NO 44
<211> LENGTH: 9
TYPE: PRT
ORGANISM: Homo sapiens
<220> FEATURE:
<223> OTHER INFORMATION:

<400> SEQUENCE: 44

Gln Leu Ser Leu Leu Met Trp Ile Thr
```